US00PP12193P2

(12) United States Plant Patent
Hanes

(10) Patent No.: US PP12,193 P2
(45) Date of Patent: Nov. 6, 2001

(54) VERBENA PLANT NAMED 'TORT WHITE'

(75) Inventor: Mitchell Eugene Hanes, Morgan Hill, CA (US)

(73) Assignee: Goldsmith Plants, Inc., Gilroy, CA (US)

( * ) Notice: Subject to any disclaimer, the term of this patent is extended or adjusted under 35 U.S.C. 154(b) by 0 days.

(21) Appl. No.: 09/378,572

(22) Filed: Aug. 20, 1999

(51) Int. Cl.[7] ..... A01H 5/00
(52) U.S. Cl. ..... Plt./308
(58) Field of Search ..... Plt./308

(56) References Cited

PUBLICATIONS

GTITM UPOVROM Citation for 'Tort White' as per QZ PBR 980464; Mar. 31, 1998.*

* cited by examiner

*Primary Examiner*—Bruce R. Campell
*Assistant Examiner*—Kent L. Bell
(74) *Attorney, Agent, or Firm*—Rothwell, Figg, Ernst & Manbeck

(57) ABSTRACT

A new and distinct cultivar of verbena plant as herein shown and described, named 'Tort White', that is characterized by its green foliage with white flowers on a prostrate branching plant; its fast rooting and vigorous growth.

2 Drawing Sheets

BACKGROUND OF THE NEW PLANT

The present invention comprises a new and distinct cultivar of verbena, botanically known as *Verbena hybrida*, and hereinafter referred to by the cultivar name 'Tort White'.

The new cultivar is propagated asexually from vegetative cuttings in Gilroy, Calif. The new cultivar originated from a seedling selected from a population made from a self-pollinated plant with the pedigree of: an unnamed plant known as 97-404-2 (unpatented).

The new cultivar was created in Gilroy, Calif., and has been repeatedly asexually reproduced by cuttings over a two-year period. The new cultivar has also been trialed at many locations in the United States and in Europe. The new cultivar has been found to retain its distinctive characteristics and reproduces true to type through successive propagations, and this novelty is firmly fixed.

DESCRIPTION OF THE DRAWING

The new verbena plant is illustrated by the accompanying photographs, the colors shown being as true as can be reasonably obtained by conventional photographic procedures.

DESCRIPTION OF THE NEW CULTIVAR

Figure 1:
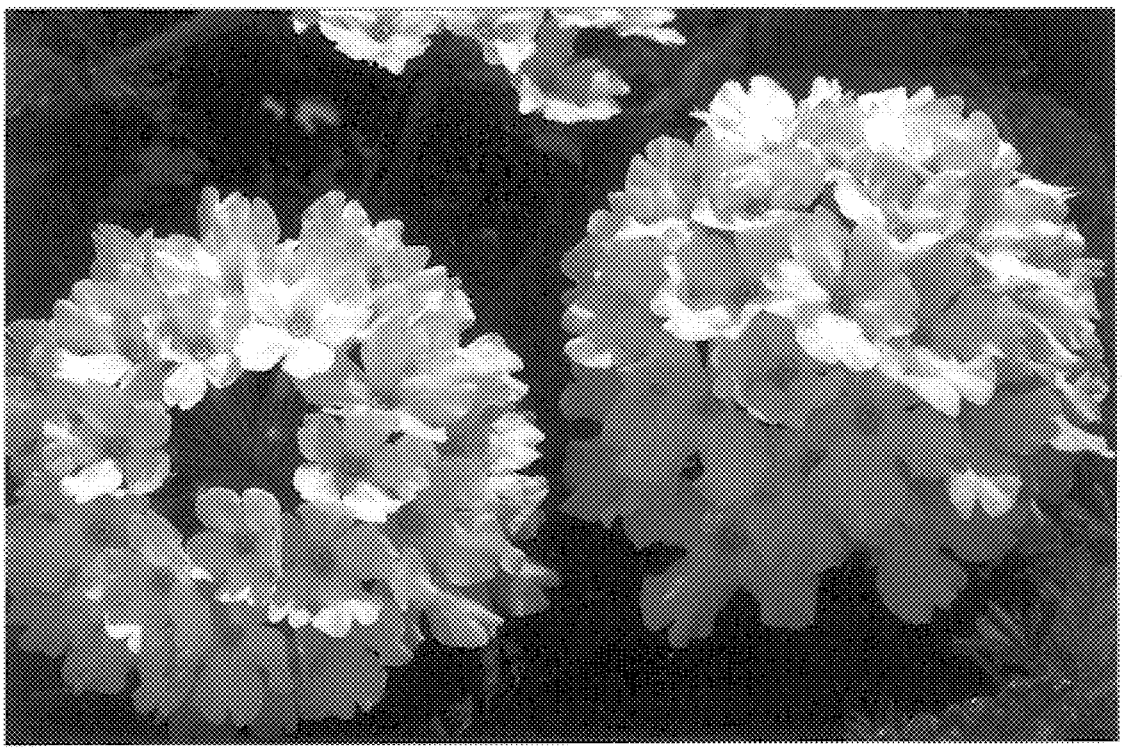
FIG. 1 depicts the inflorescence, buds and foliage.
Figure 2:
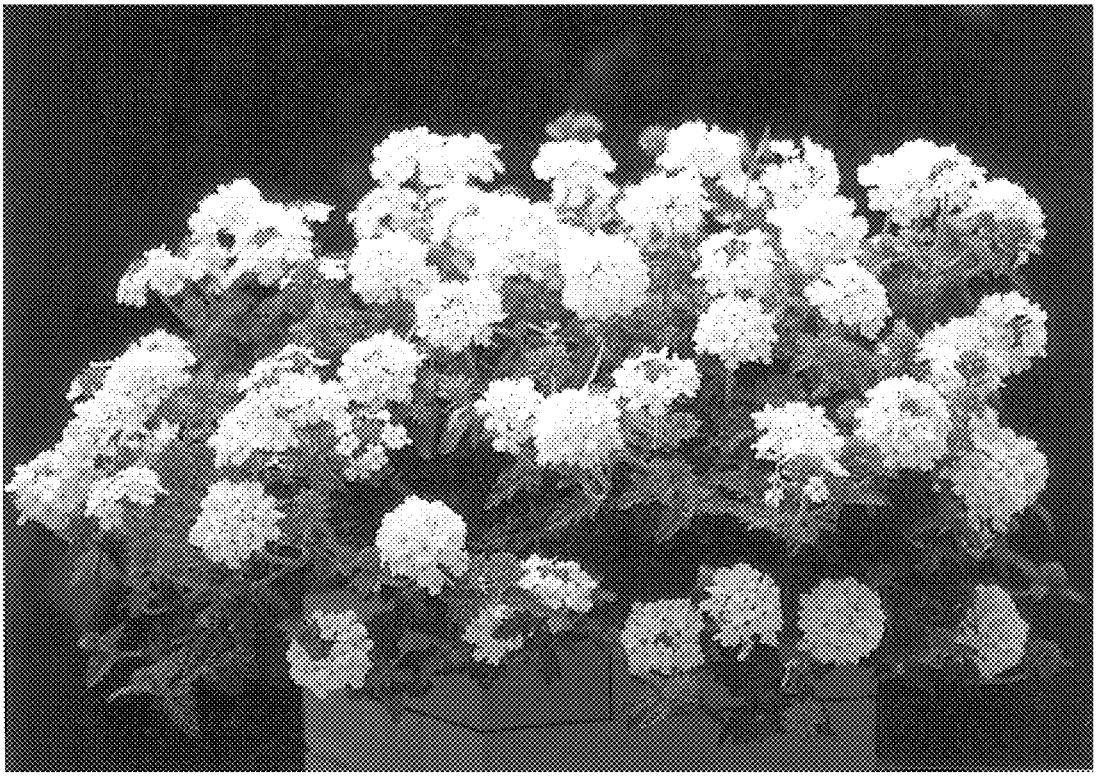
FIG. 2 shows the whole mature plant.

The following detailed descriptions set forth the distinctive characterstics of 'Tort White'. The data, which defines these characteristics, was collected from asexual reproductions carried out in Gilroy, Calif. The plant history was taken on 20-week-old plants, blossomed under natural light in a greenhouse and color readings were taken under ambient light. Color references are primarily to The R.H.S. Colour Chart of The Royal Horticultural Society of London (R.H.S.).

The Plant

Classification:

*Botanical.*—*Verbena hybrida.*

*Commercial.*—Verbena.

*Parentage.*—Unnamed plant known as 97-404-2 (unpatented).

Form: Moderately upright with prominent lateral expansion.

Height: 14 cm from soil level to top of blooms, 92 cm. wide.

Winter hardiness: Withstands temperatures to 32–34 degrees F.

Leaves:

*Length.*—4.5 cm.

*Width.*—2.1 cm.

*Texture.*—Upper surface moderately hairy; under surface slightly hairy.

Foliage:

*Shape.*—Ovate-lanceolate.

*Apex.*—Obtuse.

*Base.*—Truncate.

*Coloration.*—Upper is yellow-green RHS 147A and lower is yellow-green RHS 147B.

*Venation.*—Pinnatifid, coloration of upper is yellow-green RHS 147A, coloration of lower ribs is yellow green RHS 147C; Margin is irregularly crenately incised.

Petioles:

*Length.*—3–4 mm.

*Diameter.*—1 mm.

*Color of upper surface.*—Yellow-green RHS 147A, lower surface is yellow-green RHS 147B.

Stems:

*Length.*—18–30 cm.

*Diameter.*—2–3 mm.

*Texture.*—Pubescent.

*Internode length.*—1.0–2.5 cm.

*Color.*—Upper: Yellow-green RHS 144A. Lower: Yellow-green RHS 144B.

Roots: Initiates roots in 5 days under greenhouse conditions.

The Flower

Blooming habit: Flowers continuously throughout the year.

Period of time to produce a flowering plant: In a greenhouse, 6–8 weeks in a 4 inch pot or 8–12 weeks in a 10 inch hanging basket.

Color: White RHS 155D with a small "eye" at the base of the petals that is yellow-green RHS 145C on both sides of the petals.

Spike: Approximately 5.6 cm. diameter; depth approximately 3.5 cm.

Floret: Approximately 2.2 cm. diameter.

Petals: The corolla has a limb of five petals (lobes) fused at the base.

*Diameter of the limb.*—1.5 cm.

*Length of one lobe.*—1 cm.

*Width of one lobe.*—8 mm.

*Shape.*—Broad, obovate.

*Apex.*—Obtuse, deeply notched, base is fused to the corolla tube.

*Margin.*—Entire.

*Texture.*—Softly pubescent.

Sepals: Five fused sepals that form a calyx which sheathes the corolla tube and one smaller sepal (5 mm in length; 2–3 mm width; apex is aristate/cuspidate and base is truncate) attached to the base of the calyx.

*Length.*—1 cm.

*Width.*—5 mm.

*Shape of calyx and sepals.*—Linear.

*Apex.*—Acute.

*Color.*—Yellow-green RHS 144A for both surfaces.

Peduncles:

*Length.*—5.1 cm.

*Diameter.*—3 mm.

*Texture.*—Pubescent.

*Color.*—Yellow-green RHS 144A.

Buds:

*Length.*—1 cm.

*Diameter.*—1 mm.

*Shape.*—Linear.

*Color.*—White group RHS 155A immediately before opening.

Lastingness of the individual blooms: 5–10 days depending on environmental conditions.

Fragrance: Very slight citrusy fragrance.

Type: A spike composed of approximately 25 flowers.

Reproductive Organs

Filaments are fused with the corolla; four anthers with two pollen sacks per anther; produces a moderate amount of pollen which is light yellow RHS 11B; one stigma yellow-green RHS 144A; one style approximately 1 cm in length, somewhat transparent through the length, slightly curved at the tip with a yellow-green color RHS 145A; one pistil, one ovary which is not deeply lobed.

Fruit: Does not freely set seed but occasionally produces four narrow nutlets approximately 4 mm long; colored grey-brown RHS 199D and enclosed in the dried calyx.

Disease and Insect Resistance

No susceptibliy to diseases or insects noted to date.

Comparison with Parental Cultivar

The parental cultivar was a white-flowered verbena, however there were numerous differences. 'Tort White' has a more branched, upright spreading plant habit than the parental cultivar. 'Tort White' also is more free flowering and flowers earlier than the parental cultivar.

I claim:

1. A new and distinct Verbena plant, as illustrated and described.

* * * * *